United States Patent
Despa et al.

(10) Patent No.: US 9,687,419 B2
(45) Date of Patent: Jun. 27, 2017

(54) ASSISTED MEDICATION FILLING AND MANAGEMENT

(71) Applicant: Becton, Dickinson and Company, Franklin Lakes, NJ (US)

(72) Inventors: Mircea Despa, Cary, NC (US); Dylan Wilson, Pittsboro, NC (US); Sundeep Kankanala, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/850,631

(22) Filed: Sep. 10, 2015

(65) Prior Publication Data
US 2016/0074284 A1   Mar. 17, 2016

Related U.S. Application Data

(60) Provisional application No. 62/050,041, filed on Sep. 12, 2014.

(51) Int. Cl.
| G08B 23/00 | (2006.01) |
| A61J 7/04 | (2006.01) |
| G06F 19/00 | (2011.01) |
| G01F 23/00 | (2006.01) |

(52) U.S. Cl.
CPC ......... *A61J 7/0409* (2013.01); *A61J 7/0454* (2015.05); *A61J 7/0481* (2013.01); *G01F 23/0015* (2013.01); *G06F 19/3456* (2013.01); *A61J 2200/70* (2013.01); *A61J 2205/10* (2013.01); *A61J 2205/60* (2013.01); *A61J 2205/70* (2013.01)

(58) Field of Classification Search
CPC ....... A61J 7/0409; A61J 7/0472; G01F 23/00; G06F 19/3456

USPC .................................................. 340/573.1
See application file for complete search history.

(56) References Cited

U.S. PATENT DOCUMENTS

| 4,731,726 A | 3/1988 | Allen, III |
| 4,768,177 A | 8/1988 | Kehr et al. |
| 5,200,891 A | 4/1993 | Kehr et al. |

(Continued)

FOREIGN PATENT DOCUMENTS

| WO | WO 94/04966 A1 | 3/1994 |
| WO | WO 99/18532 | 4/1999 |
| WO | WO 99/46718 | 9/1999 |
| WO | WO 00/32098 | 6/2000 |

OTHER PUBLICATIONS

International Search Report and Written Opinion in International Application No. PCT/US15/49603, mailed on Dec. 8, 2015.

*Primary Examiner* — Tai T Nguyen
(74) *Attorney, Agent, or Firm* — Knobbe Martens Olson & Bear, LLP

(57) ABSTRACT

A medication filling and management system comprises a medication storage device for assisting patients in filling and managing medication supplies. The medication storage device includes a number of electronically monitored storage compartments and a communication system to identify a medication to be provided from an adjacent medication commercial package, automatically identify to a user which compartments of the storage device are to be filled with the identified medication from the commercial package, and detect and communicate the filling and dispensing of the medication from the storage device.

26 Claims, 17 Drawing Sheets

(56) References Cited

U.S. PATENT DOCUMENTS

| | | | |
|---|---|---|---|
| 5,408,443 A * | 4/1995 | Weinberger | G06F 19/3462 221/3 |
| 5,642,731 A | 7/1997 | Kehr | |
| 5,897,493 A | 4/1999 | Brown | |
| 5,954,641 A | 9/1999 | Kehr et al. | |
| 5,997,476 A | 12/1999 | Brown | |
| 6,024,699 A | 2/2000 | Surwit et al. | |
| 6,101,478 A | 8/2000 | Brown | |
| 6,102,855 A | 8/2000 | Kehr et al. | |
| 6,161,095 A | 12/2000 | Brown | |
| 6,168,563 B1 | 1/2001 | Brown | |
| 6,169,707 B1 * | 1/2001 | Newland | A61J 7/0481 221/2 |
| 6,294,999 B1 | 9/2001 | Yarin et al. | |
| 7,158,011 B2 * | 1/2007 | Brue | A61J 7/0481 340/309.16 |
| 7,369,919 B2 | 5/2008 | Vonk et al. | |
| 8,417,381 B2 | 4/2013 | Vonk et al. | |
| 2003/0052135 A1 * | 3/2003 | Conley | A61J 7/0472 221/258 |
| 2004/0138921 A1 | 7/2004 | Broussard et al. | |
| 2010/0101317 A1 | 4/2010 | Ashrafzadeh et al. | |
| 2014/0156064 A1 * | 6/2014 | Crawford | G06F 19/3462 700/236 |
| 2014/0262918 A1 * | 9/2014 | Chu | A61J 1/03 206/534 |
| 2015/0048102 A1 * | 2/2015 | Dickie | A61J 1/03 221/2 |

\* cited by examiner

ASSISTED MEDICATION FILLING AND MANAGEMENT

CROSS-REFERENCE TO RELATED APPLICATIONS

This application claims priority to U.S. Provisional Patent Application Ser. No. 62/050,041 filed on Sep. 12, 2014 and entitled "Assisted Medication Filling and Management", the content of which is hereby incorporated by reference in its entirety.

FIELD OF THE INVENTION

The present invention relates to a medication filling and management system comprising a medication storage device for assisting patients in filling and managing medication supplies. The medication storage device includes a number of electronically monitored storage compartments and a communication system to identify a medication to be provided from an adjacent commercial package, automatically identify to a user which compartments of the storage device are to be filled with the identified medication from the commercial package and detect the filling and dispensing of the medication from the storage device.

BACKGROUND OF THE INVENTION

Many patients with chronic conditions have difficulty adhering to prescribed therapies. In general, the more medications taken and the more times each day that patients must use various therapies, the more likely there will be a medication error. Often patients have co-morbid conditions that interfere with their adherence to medication regimens. These conditions may include diabetes and associated complications such as blindness or lack of mobility, various neurological conditions and dementias, arthritis and associated difficulties in manipulating devices, and other debilitating conditions. The interactions of various co-morbidities can bring additional complexity and dynamism to medication regimens. Cognition also generally declines with age. Consequently, elderly patients may experience difficulty filling and organizing their medications, and remembering to take them as prescribed. These problems are widely recognized, but there have been no cost-effective solutions to date.

Several solutions to the above problems have been proposed. One category of solutions includes the provision of devices that monitor when the cap of a prescription pill bottle has been removed. This information is stored electronically and may be uploaded to a data network using a remote docking station. This method is convenient for a few medications, but difficult with many medications. In addition, the individual devices are relatively expensive. Aprex's (www.aardex.com) smart pill bottle cap is an example of such a device.

Another category of solutions include the provision of devices related to vending machine concepts. These devices contain a plurality of medications and dispense them at an appropriate time specified by internal software and hardware systems. Few of these devices have been commercialized since they are relatively expensive to manufacture and have limited capacity for various medications. The reliability of these devices in a remote setting is also questionable. The e-pill MD.2 Monitored Automatic Medication Dispenser (www.epill.com) is an example of such a device, although it only dispenses a single medication container.

A third category of solutions include the provision of devices that use a tray which is inserted into a portable device. These trays may be filled with medications as needed. The MEDGlider (www.informedix.com) is an example of such a device. This device has limited capacity for patients with chronic conditions. Also, since the medication tray is not identified to the main device, there may be confusion over which tray should be placed in the device. Finally, this device does not include a medication package that contains all the medications to be taken at a single time. That is, patients using this device must remove each medication sequentially as they are reminded to by systems contained in the main device. This long sequence of taking multiple medications limits the number of patients willing to use this device to those with relatively simple conditions, good cognition and strong motivation.

A fourth category of solutions include the provision of medication management devices, such as organizer/reminder devices. Typically, these devices use small trays or compartments and the patient fills the device as needed. The devices are then self-programmed by patients to remind them to take medications at a specific time. When patients either self-program or self-fill the device, errors can occur. These errors become more common as the complexity of the medication regimen increases. Further, conventional organizer/reminder devices do not prevent these kinds of errors. Since these devices do not assist the user with identifying the medication, do not record or monitor medication usage, and are not connectable to an outside service or information provider, they have limited positive effect on medication adherence.

A fifth category of solutions include the provision of pill containers which contain radio frequency (RF) tags that are sensed on a platform. An example of such a device is disclosed in commonly-assigned U.S. Pat. No. 6,294,999, U.S. Pat. No. 7,369,919, and U.S. Pat. No. 8,417,381, the entire contents of each being incorporated herein by reference. These devices may contain a large number of pill containers on the device, but each pill container is placed individually on the device. This creates some difficulty for the patients using these devices since they have to place a large number of various sized containers randomly on the device; there is also some potential that some containers will be lost. An additional limitation of this approach is the need to fill a large number of medication containers with a number of different medications all taken at a specific time by the patient. These containers must be filled with a high degree of accuracy and precision. In addition, labeling of containers that contain many medications is difficult since the containers may not be large enough to hold a legible label listing required information for each medication in the pill container.

Other commonly-assigned U.S. patents and published international (PCT) applications disclosing related subject matter are listed below, the entire contents of each being incorporated herein by reference.

4,731,726
4,768,177
5,200,891
5,642,731
5,897,493
5,954,641
5,997,476
6,024,699
6,101,478
6,102,855

-continued

| |
|---|
| 6,161,095 |
| 6,168,563 |
| WO 99/18532 |
| WO 99/46718 |
| WO 00/32098 |

Accordingly, a need exists for a system and method to automatically identify a medication to be provided from an adjacent commercial package, identify to a user which compartments of the storage device are to be filled with the identified medication from the commercial package and detect the filling and dispensing of the medication from the storage device.

SUMMARY OF THE INVENTION

It is therefore an object of embodiments of the present invention to provide a system and method to automatically identify a medication to be provided from an adjacent commercial package, identify to a user which compartments of the storage device are to be filled with the identified medication from the commercial package and detect the filling and dispensing of the medication from the storage device.

It is another object of embodiments of the present invention to provide a medication storage device wherein medications are placed into storage compartments of the storage device, and the compartments are individually addressable both physically and electronically.

It is another object of embodiments of the present invention to provide a medication storage device wherein the compartments are individually identifiable both physically and electronically, such as through the provision of lights.

It is another object of embodiments of the present invention to provide a medication storage device wherein the compartments include covers, and physical or electronic sensors to detect opening and closing of the covers.

It is another object of embodiments of the present invention to provide a medication storage device wherein the compartments include electronic sensors to detect content of the compartment.

It is another object of embodiments of the present invention to provide a medication storage device provided with communication systems to obtain, maintain and communicate information about the medications, their location on the tray, and when they are to be taken.

It is another object of embodiments of the present invention to provide a medication storage device wherein the storage device can communicate with an adjacent medication commercial package using for example, barcode reading and/or radio-frequency identification (RFID) technology to obtain information about the medication in the adjacent medication commercial package.

It is another object of embodiments of the present invention to provide a medication storage device wherein the storage device can communicate with an adjacent other device for example, a smart phone, tablet, pager, cell phone, interactive video device and conventional telephone for bidirectional data exchange and communications.

It is another object of embodiments of the present invention to provide a medication storage device wherein the storage device can communicate with a remote other device for example, a server for bidirectional data exchange and communications.

It is another object of embodiments of the present invention to provide a medication storage device wherein the storage device can communicate and then calculate and identify a prescription regime, calculate and identify compartments in which to place a medication or remove a medication, calculate and communicate adherence to a prescription regime, and store and update data related to each.

It is another object of embodiments of the present invention to provide a medication storage device wherein the storage device can communicate with, and be placed into a filling station.

These and other objects are substantially achieved by providing, in accordance with embodiments of the present invention, a medication filling and management system comprising a medication storage device for assisting patients in filling and managing medication supplies. The medication storage device includes a number of electronically monitored storage compartments and a communication system to identify a medication to be provided from an adjacent medication commercial package, automatically identify to a user which compartments of the storage device are to be filled with the identified medication from the commercial package, and detect and communicate the filling and dispensing of the medication from the storage device.

According to one embodiment of the present invention, a medication storage system is provided. The medication storage system includes a medication storage container including a plurality of storage compartments for receiving one or more medications, and one or more indicators, each indicator configured to indicate one of the plurality of storage compartments. The medication storage system further includes an identification sensor configured to detect medication information and a processor configured to determine a medication regimen based on the detected medication information, the medication regimen including one or more doses and, for each dose, a time at which to be taken, and activate one or more of the indicators based on the determined medication regimen.

According to another embodiment of the present invention, an electronic method for operating a medication storage container is provided. The electronic method for operating a medication storage container includes receiving medication information, determining by a processor a medication regimen based on the received medication information, the medication regimen including one or more doses and, for each dose, a dosage time, and activating one or more indicators on a medication storage container based on the determined medication regimen, the medication storage container including a plurality of storage compartments for receiving one or more medications, wherein each indicator is configured to indicate one of the plurality of storage compartments.

According to another embodiment, a medication storage container is provided. The medication storage container includes a transceiver configured to wirelessly connect with one or more electronic devices, a plurality of storage compartments for receiving one or more medications, and one or more indicators, each indicator configured to indicate one of the plurality of storage compartments, the indicators configured to indicate one or more storage compartments in which to fill medication, the indicators further configured to indicate one or more storage compartments at a time at which the medication in the one or more storage compartments is to be taken.

BRIEF DESCRIPTION OF THE DRAWINGS

The above and other objects and advantages will become apparent upon consideration of the following drawings and detailed description. The preferred embodiments of the present invention are illustrated in the appended drawings in which like reference numerals refer to like elements and in which:

FIGS. 1(a) to 1(m) illustrate a medication storage device in accordance with an embodiment of the invention;

In the drawing figures, it will be understood that like numerals refer to like structures.

DETAILED DESCRIPTION OF THE PREFERRED EMBODIMENT

Figure 1A:
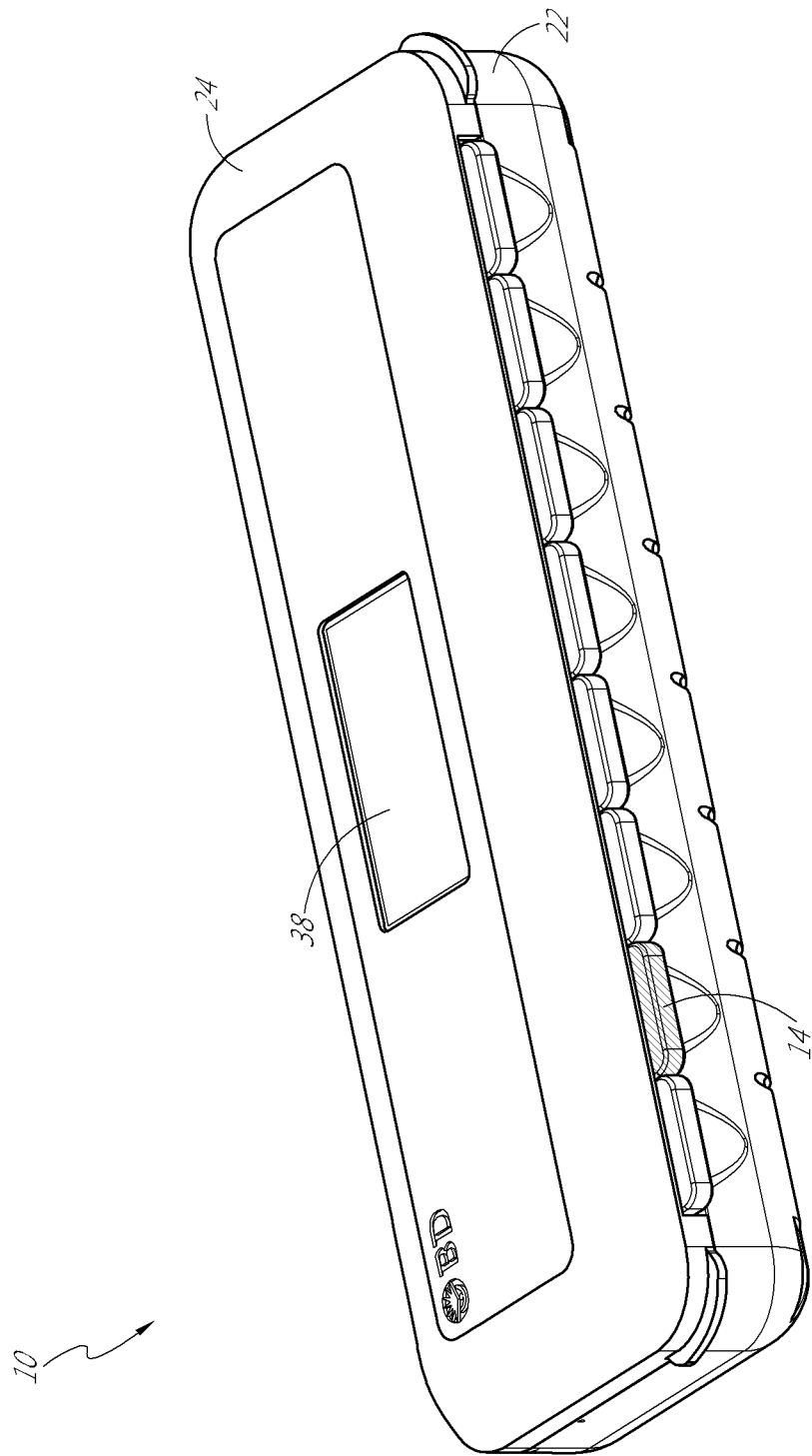

The various features of the preferred embodiments will now be described with reference to the drawing figures, in which like parts are identified with the same reference characters. The following description of the presently contemplated best mode of practicing the invention is not to be taken in a limiting sense, but is provided merely for the purpose of describing the general principles of the invention.

The proposed invention relates to medication adherence technology to help patients with complex medication regimens. Specifically, the proposed invention relates to a device with compartments for each medication taking event (e.g., Monday, Breakfast on Monday, and so forth). Each compartment is individually addressable and can be identified by a light or other technology to indicate to a user a single compartment as the one of interest at any given time.

FIGS. 1(a) to 1(m), illustrate such a medication storage device 10 in accordance with an exemplary embodiment of the invention. The medication storage device 10 contains one or more compartments 12 for receiving and dispensing medications. For purposes of the following description, the user can manually place medications from a commercial package into the compartments 12, or an automatic filling device can automatically place the medications in the compartments such as when the storage device 10 is placed into a filling station.

Figure 1B:
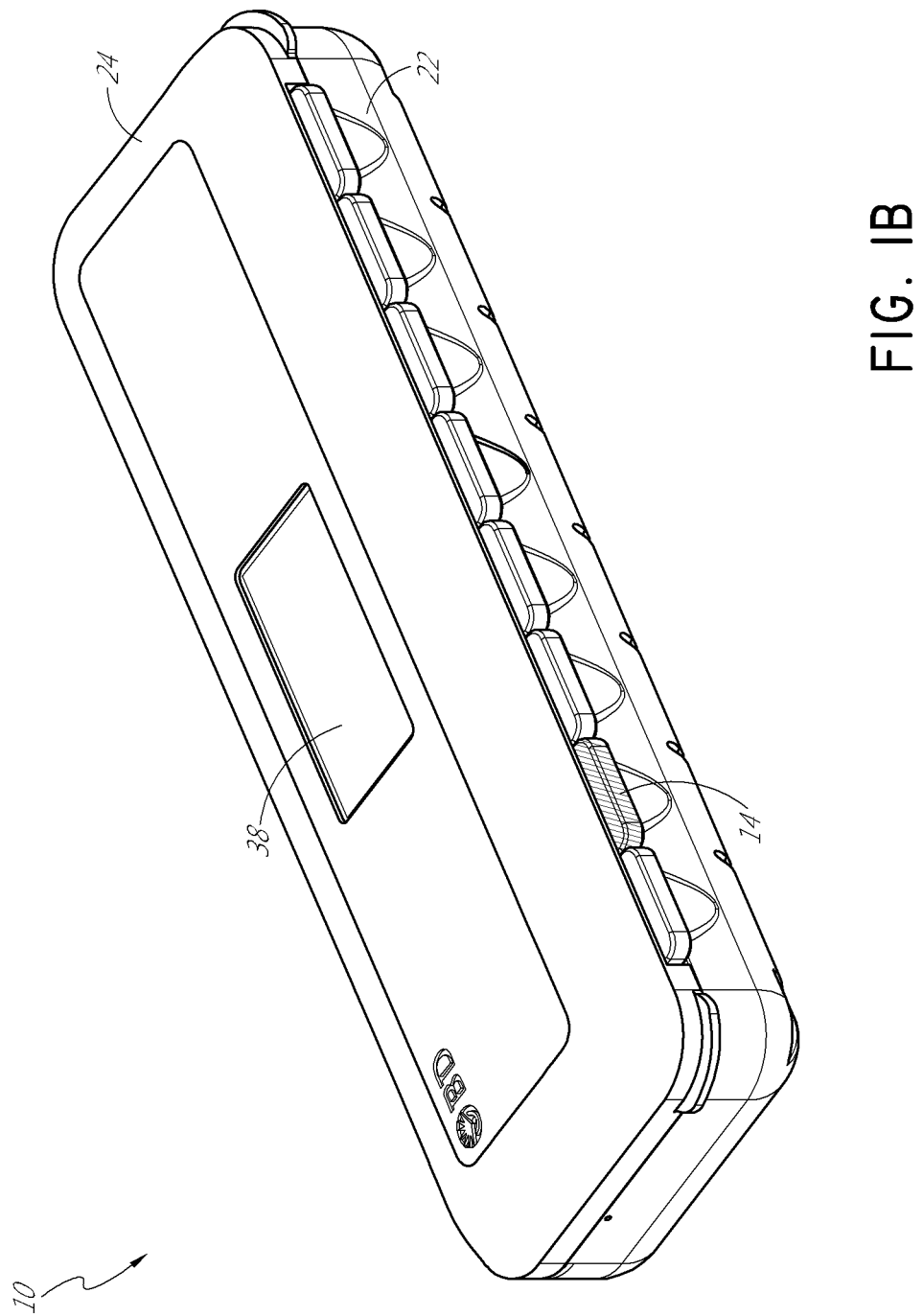
Figure 1C:
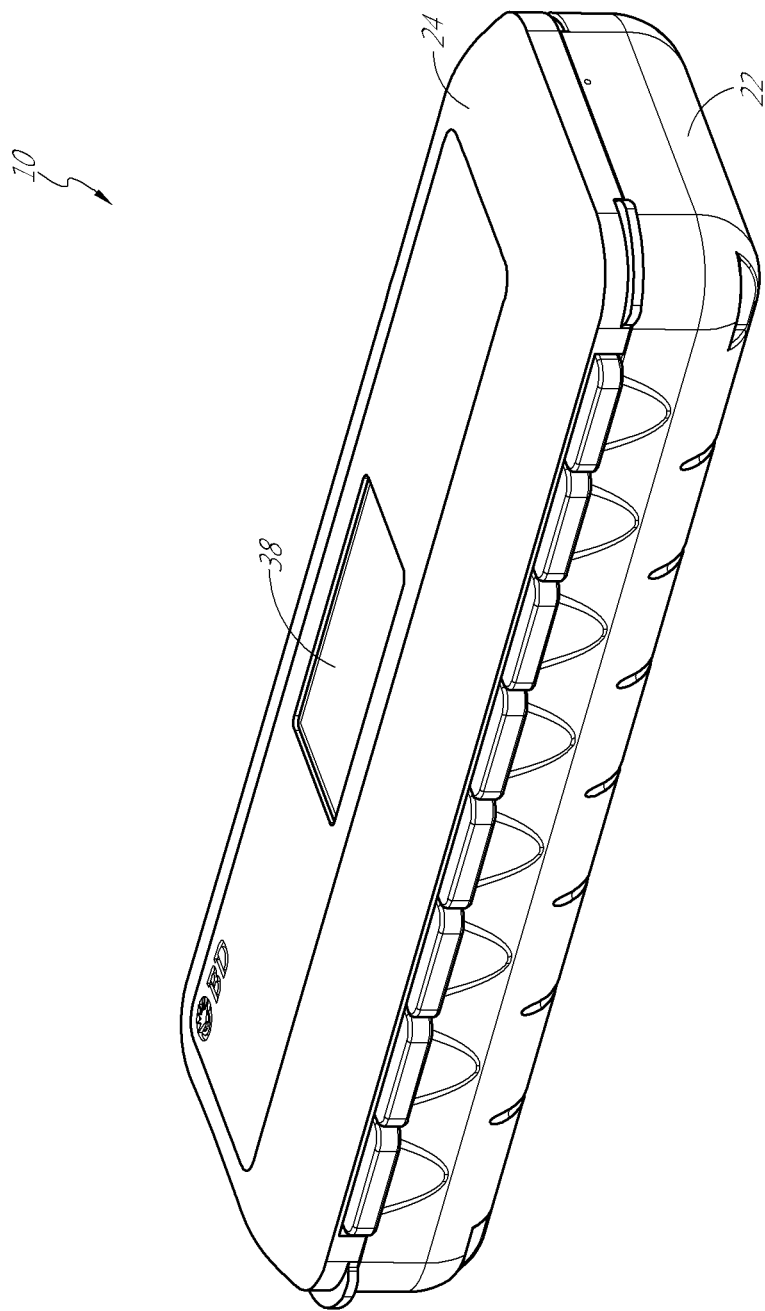
Figure 1D:
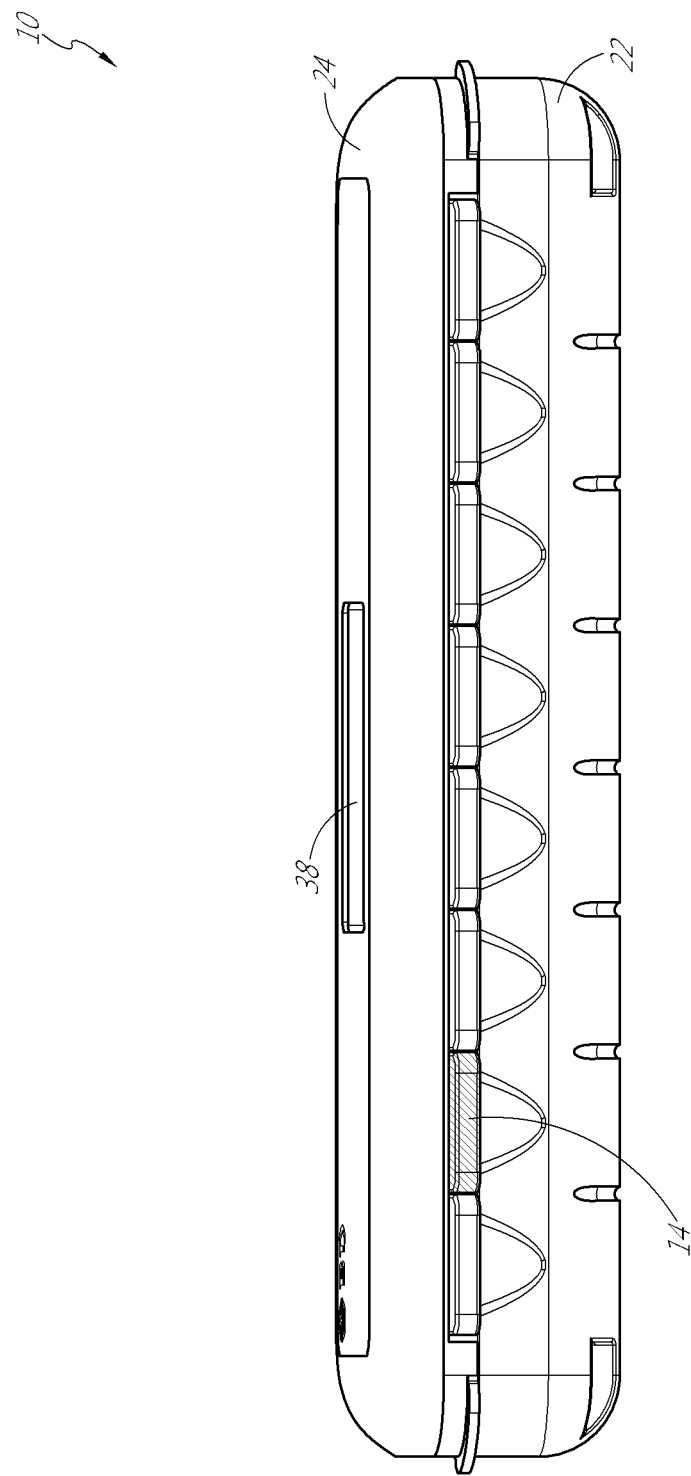
Figure 1E:
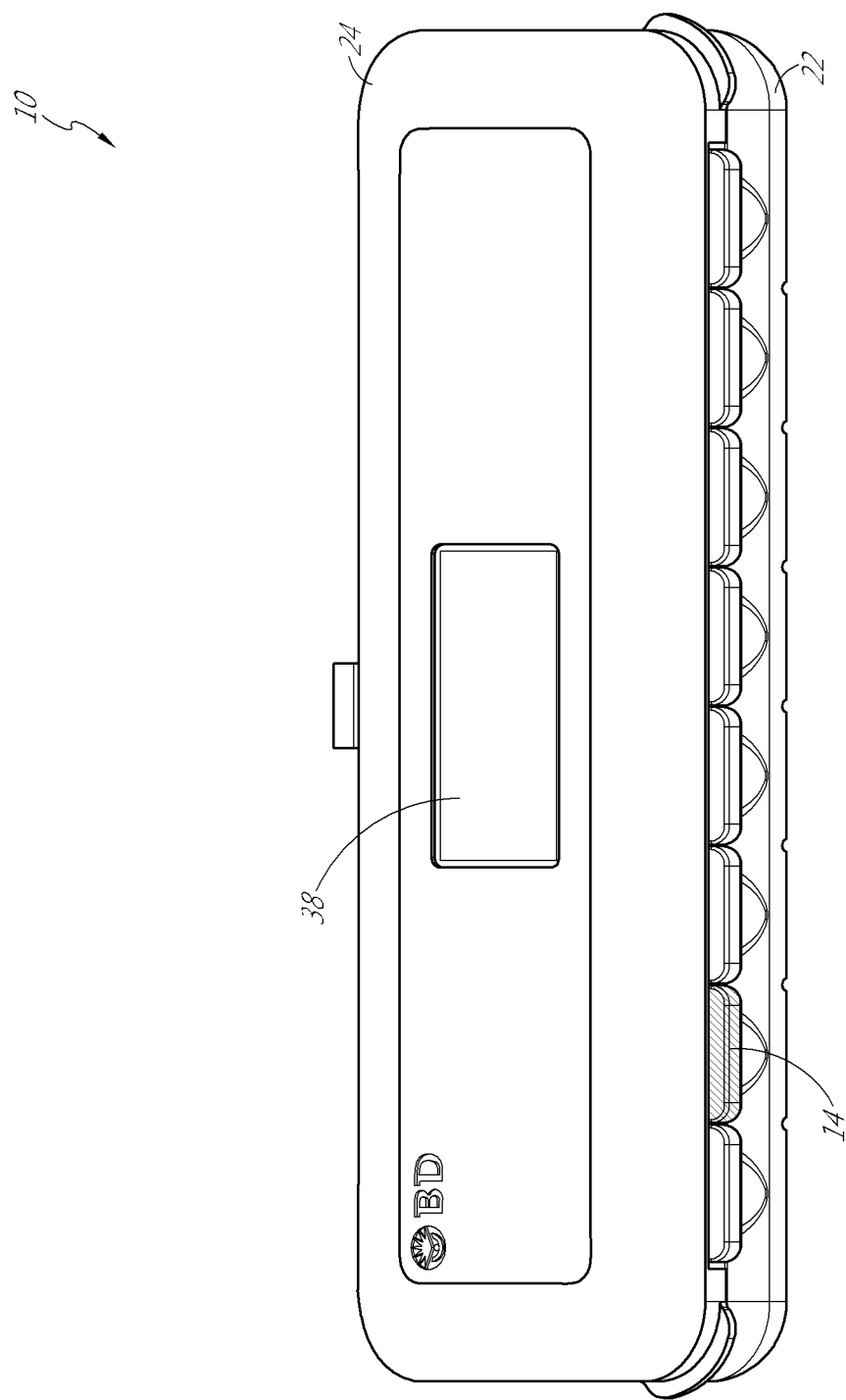
Figure 1F:
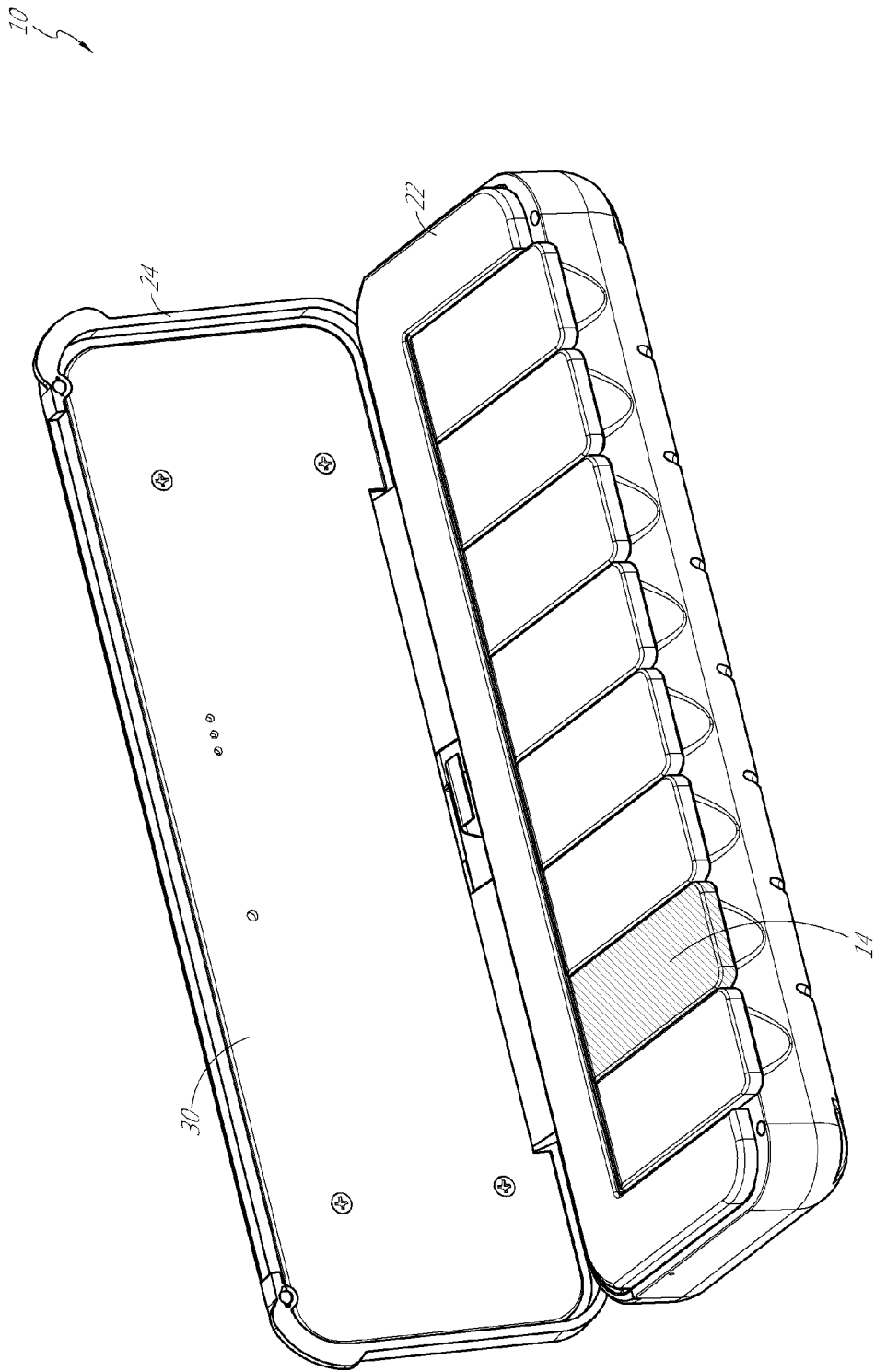
Figure 1G:
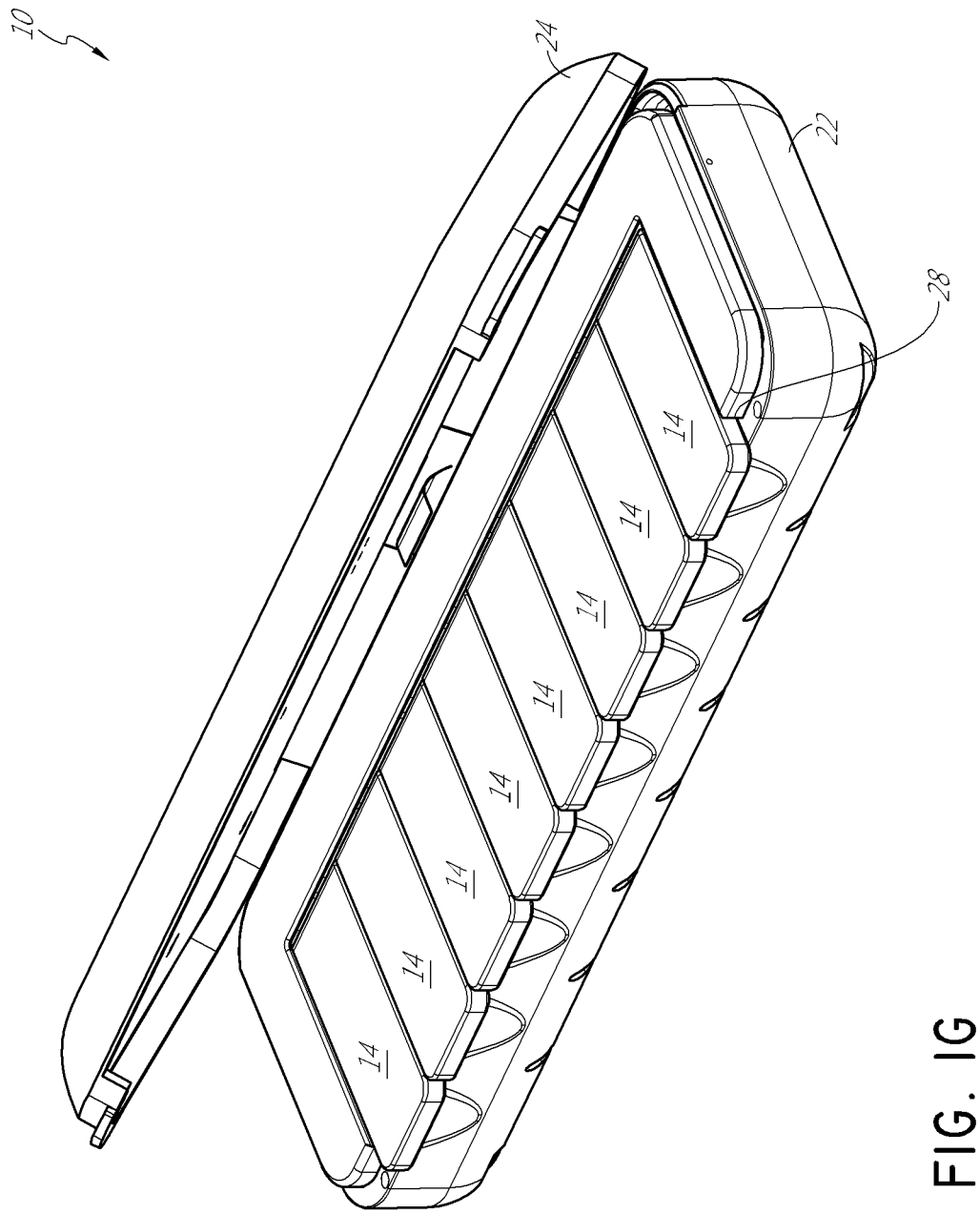
Figure 1H:
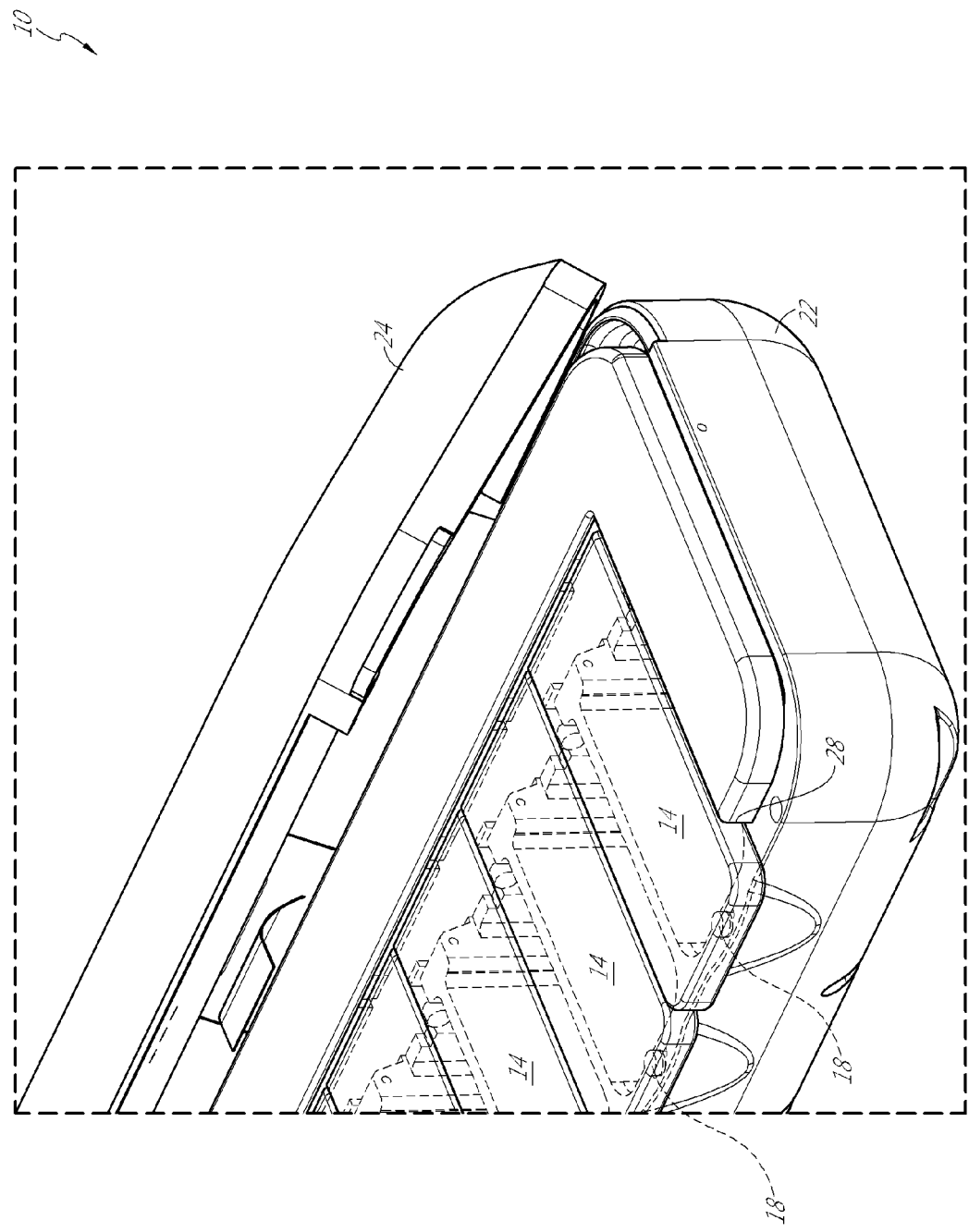
Figure 11:
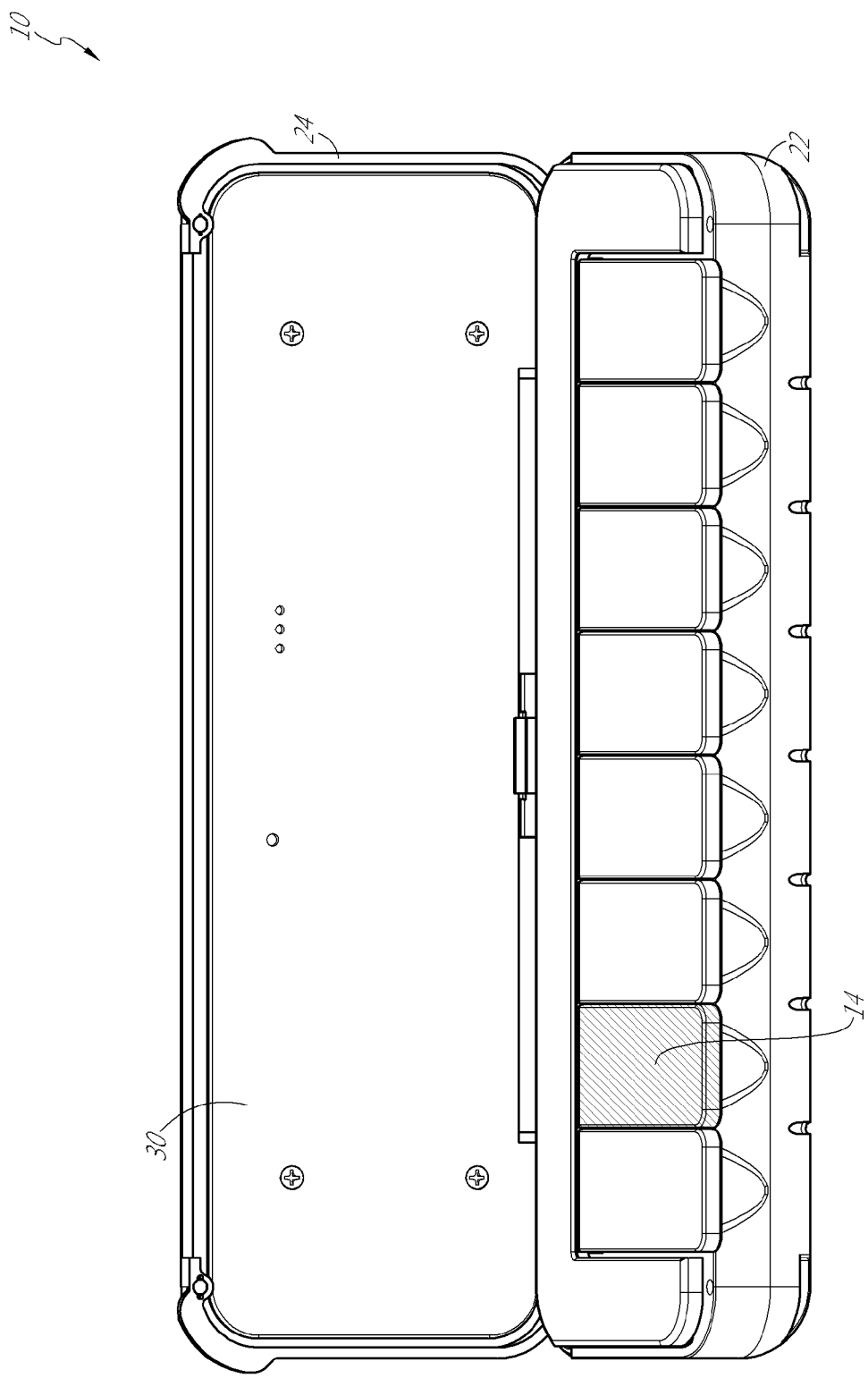
Figure 1J:
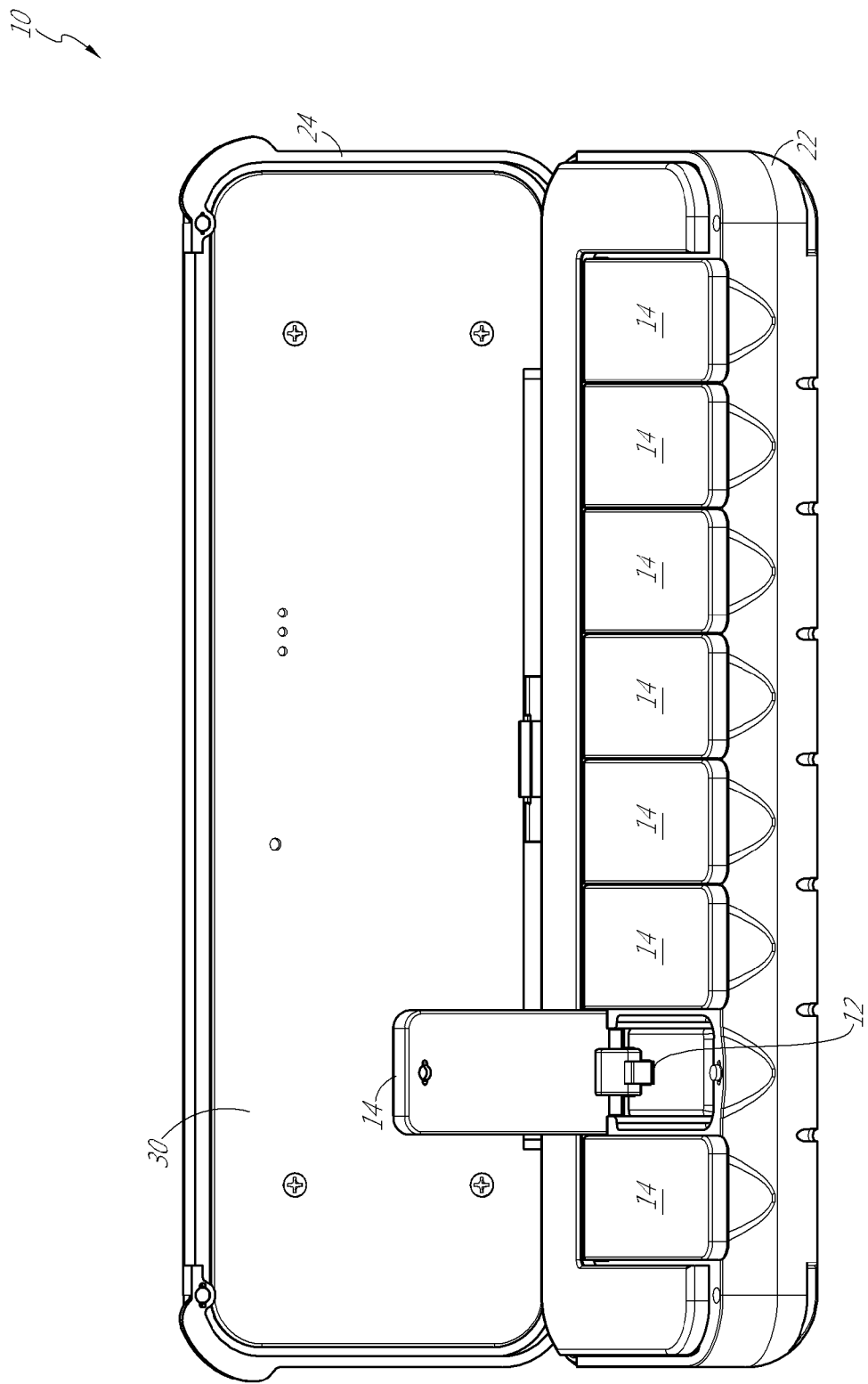
Figure 1K:
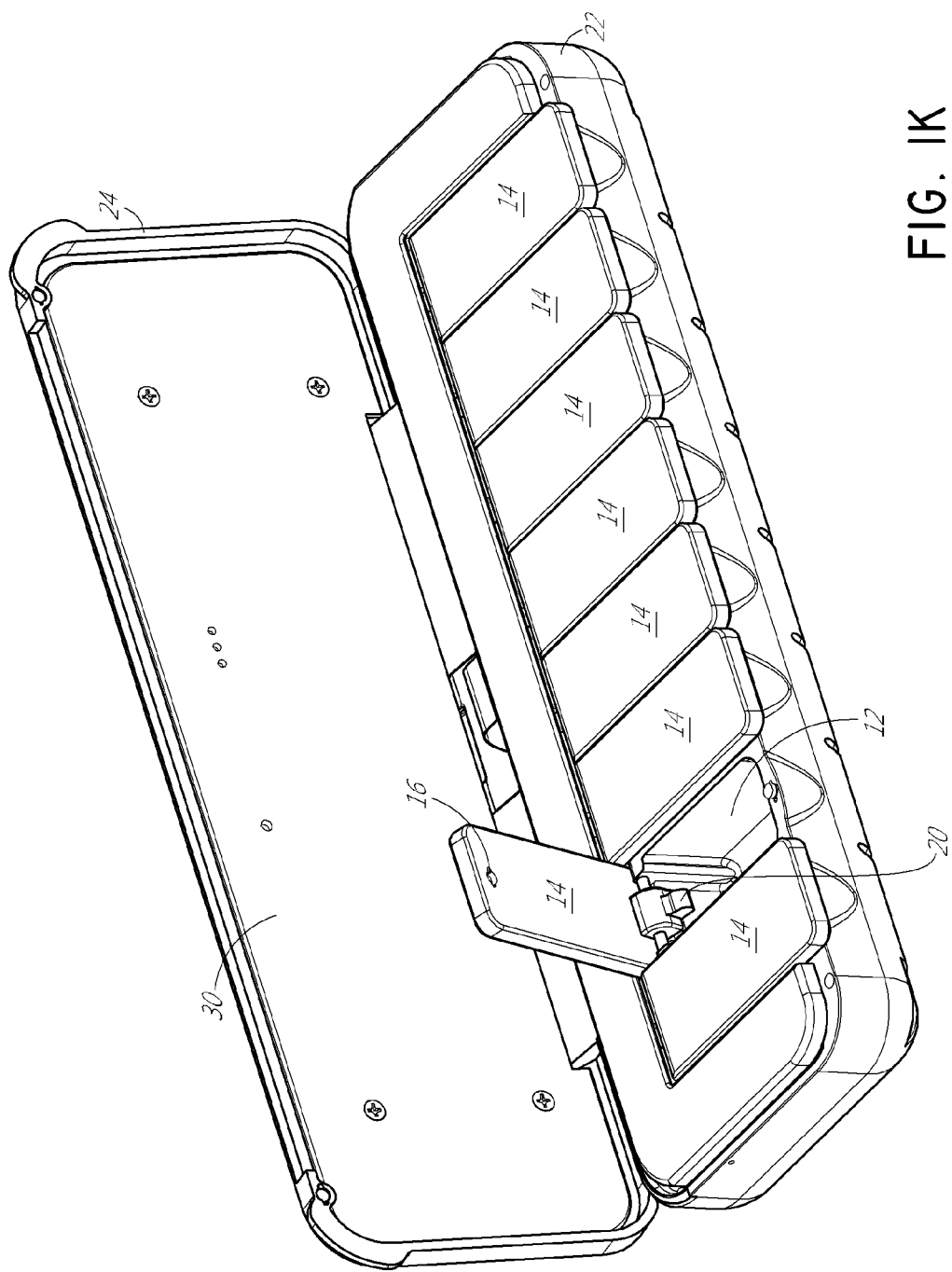
Figure 1L:
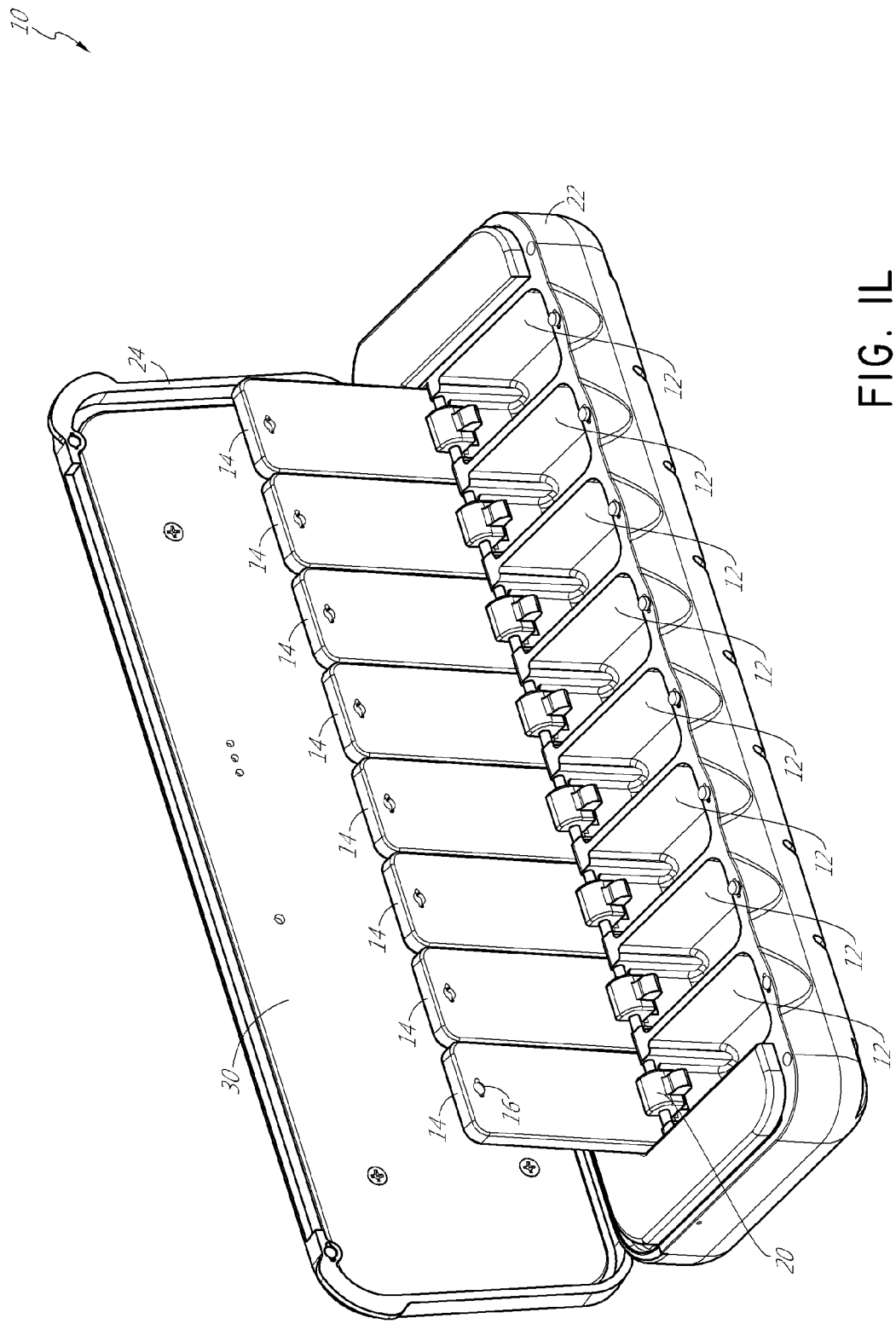
Figure 1M:
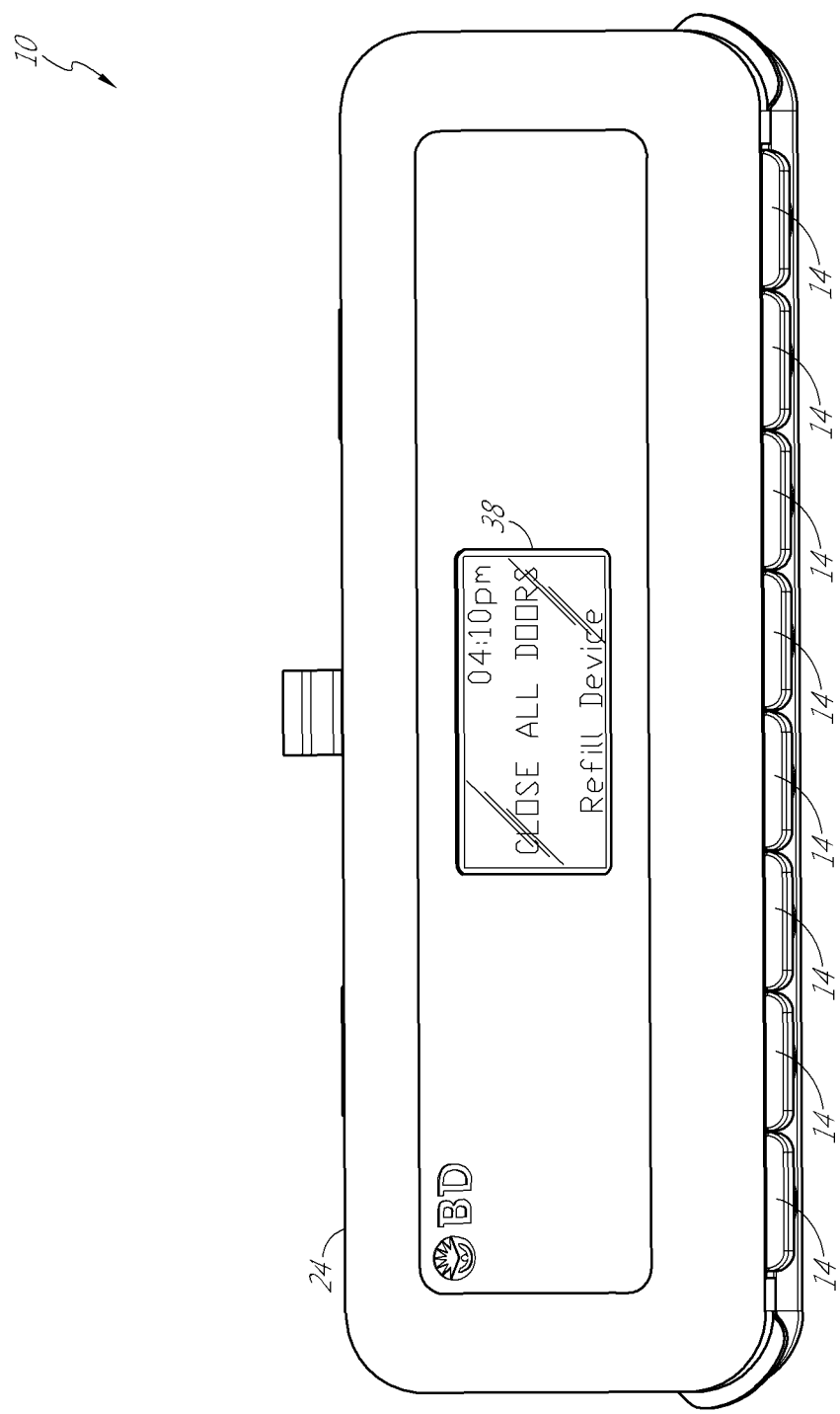

In an exemplary embodiment, the storage device 10 comprises a plurality of covered compartments 12 arranged within a body 22, and shaped in any number of desired fashions, but are not limited to the arrangements and shapes shown. Each compartment 12 is provided with a cover 14, and the body 22 is provided with a cover 24. FIGS. 1(a) to 1(m) illustrate such a medication storage device 10 in accordance with an exemplary embodiment of the invention. FIGS. 1(a), 1(b) and 1(d) are front perspective views, and FIG. 1(c) is a rear perspective view of the medication storage device 10 in accordance with an exemplary embodiment of the invention. FIGS. 1(e) and 1(m) are top perspective views, and FIGS. 1(f), 1(g), 1(h) and 1(i) are perspective views of the medication storage device 10 with the body cover 24 in an open position in accordance with an exemplary embodiment of the invention. FIGS. 1(j), 1(k) and 1(l) are perspective views of the medication storage device 10 with the body cover 24 and one or more of the compartment covers 14 in an open position in accordance with an exemplary embodiment of the invention.

Each compartment 12 comprises a user-removable lid or cover 14 which can be hinged or otherwise secured to the compartment 12 or body 22 using a barrel or living hinge, and can be opened and closed using a press-fit or interference fit, or using a securing detent 16 on either the compartment 12 or the cover 14. The cover 14 can be colored, numbered, labeled, shaped or otherwise physically identifiable to the user. Still further, each cover 14 can be clear to show the content of the compartments 12, or colored to transmit and disperse an illumination provided by a light emitting source as described in greater detail below.

Figure 2:
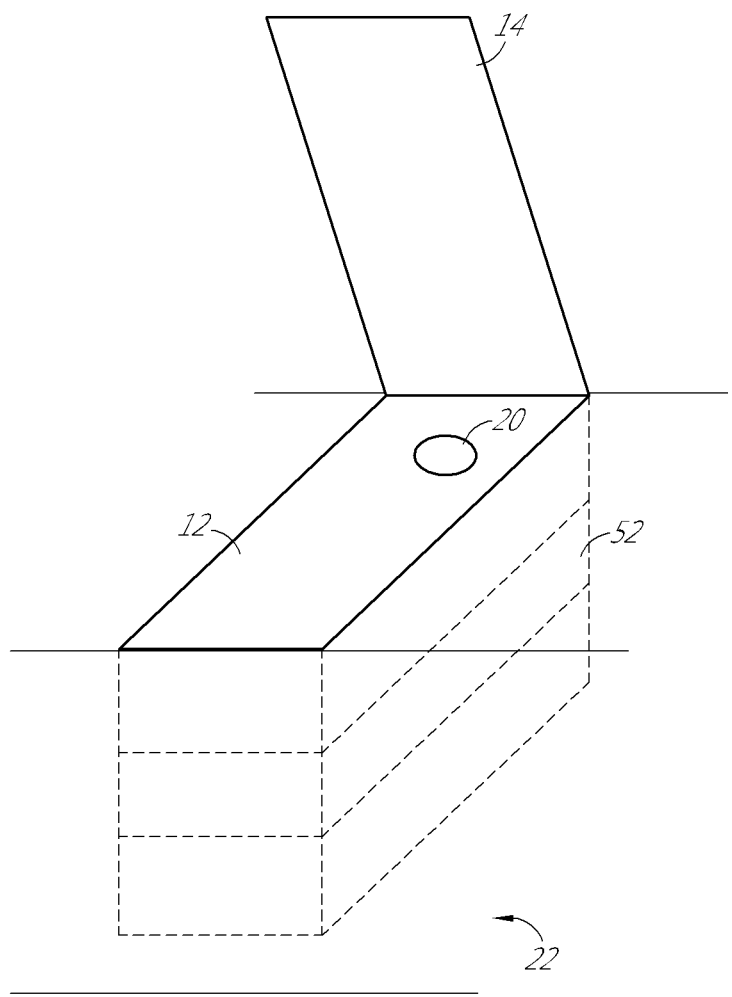
FIG. 2 illustrates a perspective view of a storage compartment of the medication storage device in accordance with an embodiment of the invention.

Each compartment 12 as shown in greater detail in FIG. 2 can further comprise an electronic switch or content sensor 52 adjacent to or surrounding the respective compartment to detect a content level in the respective compartment 12. FIG. 2 illustrates a perspective view of a storage compartment 12 of the medication storage device 10 in accordance with an embodiment of the invention. Each compartment 12 can further comprise an electronic switch or cover sensor 18 to detect opening and closing of the covers 14. The technologies of such switches, content sensors and cover sensors, such as mechanical switches and optical sensing devices such as silicon photodiodes or CCDs, are known to those skilled in the art and therefore, detailed descriptions thereof are omitted.

Each compartment 12 can further comprise a light emitting source 20 within, adjacent to or surrounding the respective compartment to draw user attention to the respective compartment when illuminated. In one embodiment, a light emitting source 20 can be disposed adjacent to the hinge of each cover 14 and can be provided to work in cooperation with the cover 14 such that when activated, the entire cover 14 is illuminated and still further, illuminated with a desired color either as configured by the light emitting source 20 or by the materials of the cover 14. An example of such an illuminated cover 14 is shown in FIGS. 1(f) and 1(i).

A separate cover 14, content sensor 52, cover sensor 18 and light emitting source 20, is preferably provided for each respective compartment 12, and are individually monitored and controlled as described in greater detail below. Visual cues provided by the light emitting source 20 to identify individual compartments 12 can include the use of light emitting diodes or lasers of various colors, and light pipe configurations on the medication storage device 10. Organic diodes and electroluminescent methods can also be convenient and low-cost methods of identifying individual compartments 12.

In addition to light emission, the use of sound, shape and color can also assist patients as they take medications. Each compartment 12 can be substantially rectangular shaped, and can have an enclosed and/or raised bottom to ease removal of the content therein by the user. The interior of the compartment 12 can be any suitable color, such as those that may ease the identification of contents therein either separately, or in cooperation with operation of the light emitting source 20.

The compartments 12 are assembled and secured to one another within a body 22 of the storage device 10 in a substantially tray-shaped configuration, but embodiments are not limited thereto. The body 22 is provided with a cover 24 which can be hinged or otherwise secured to the body 22 using a barrel or living hinge, and can be opened and closed using a press-fit or interference fit, or using a securing detent 26 on either the body 22 or the cover 24. The cover 24 can be colored, numbered, labeled, shaped or otherwise physically identifiable to the user. Still further, the cover 24 can be clear to show the content of the body 22, and can include a display 38.

As shown, a series of compartments 12 are aligned within the body 22. The cover 14 of each compartment 12 is configured to independently open and close when the cover 24 of the body 22 is opened. Each cover 14 is secured at one end by the hinge, and extends to an opposite end that extends from within the body 22 when closed. To do so, the front of the body 22 includes a slotted portion 28 which receives a user-graspable end of each cover 14 when each cover 14 is closed, and which remains visible when the cover 24 is closed. When the covers 14 and 22 are closed and the light emitting source 20 near the hinge of each cover is activated, the material of the cover 14 transmits the emitted light throughout the respective cover 14 and to the user-graspable end of each cover 14 which is visible in the slotted portion 28 even when the covers 14 and 22 are closed. Accordingly, when the covers 14 and 22 are closed and the light emitting source 20 near the hinge of a respective cover is activated, a user can identify the compartment 12 of interest by detecting the lighted user-graspable end of the respective cover 14 which is visible in the slotted portion 28. An example of such an illuminated user-graspable end of the respective cover 14 is shown in FIGS. 1(*a*), 1(*b*), 1(*d*) and 1(*e*). When the cover 22 is then opened, the user can confirm the identity of the compartment 12 of interest by detecting the lighted respective cover 14. An example of such an illuminated respective cover 14 is shown in FIGS. 1(*f*) and 1(*i*).

In these or other exemplary embodiments, the body 22, compartments 12 and covers 14 and 24, can be constructed of any suitable materials that are compatible with the storage of medications such as molded plastic, but are not limited thereto. Further, as described in greater detail below, the storage device 10 can be shaped for use with a prescription filling station.

The medication storage device 10 also contains a communication and data processing system 30 within the body 22 and cover 24 such that the storage device 10 can communicate with an adjacent medication container using for example, barcode reading and/or radio-frequency identification (RFID) technology to obtain information about the medication in the adjacent medication container. For example, a user may receive a prescription or prescription refill from a doctor or pharmacy and wish to transfer the contents from the commercial package to the compartments 12 of the medication storage device 10. One step in doing so is providing an automatic and electronic communication between the medication storage device 10 and the commercial package. The commercial package is often provided with a barcode, quick response code, identification number or RFID chip (including low-bit tags) to identify the contents, and content and prescription regimen information, which can be scanned and interpreted by the communication and data processing system 30 of the storage device 10. To do so, the communication and data processing system 30 of the storage device 10 comprises at least a scanning or communicating element to scan or otherwise interpret a barcode, quick response code, identification number or RFID chip of the commercial package when placed adjacent to the storage device 10, and process the information with or without additional information obtained by still other communications with other local devices 40, such as a smart phone, tablet, pager, cell phone, interactive video device and conventional telephone, or remote devices 60, such as a server.

The storage device 10 also consists of enough computing and wireless communications capacity necessary to communicate with other local and remote device(s) 40 and 60 to access information about the medication regimen and report adherence results. Software tools can be used to manage medications, and special processes can be used to ensure high quality in the filling and dispensing process. In this preferred embodiment, multiple prescription patients would be the most advantageous users of the medication adherence system. As the storage device 10 is loaded with prescription drugs, data about each prescription drug is loaded into the storage device 10 and is subsequently used to direct the filling of the compartments 12, and to direct the dispensing of the contents of the compartments 12.

Figure 3:
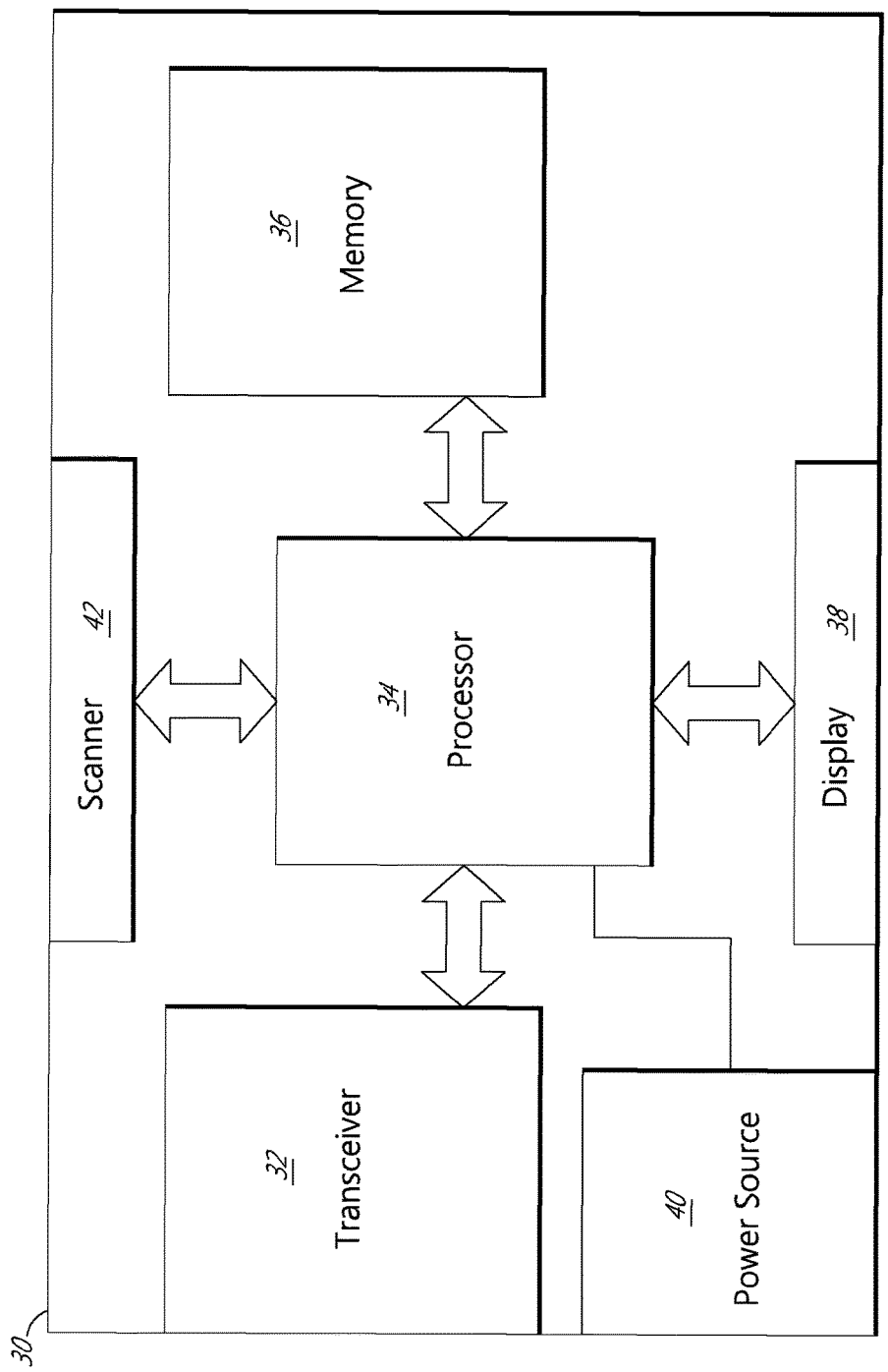
FIG. 3 is a block diagram of a communication system of the medication storage device in accordance with an embodiment of the invention.

FIG. 3 is a block diagram of the communication and data processing system 30 of the storage device 10 in accordance with an embodiment of the invention. The communication and data processing system 30 comprises a transceiver 32 for wireless communications, connected to a processor 34, memory 36, display 38, and power source 40, such as a rechargeable cell, standard alkaline cell, or similar type cell. A scanning or communicating element 42 is also provided to scan or otherwise interpret a barcode, quick response code, identification number or RFID chip of the commercial package 50 when placed adjacent to the storage device 10 as illustrated in FIG. 4.

As noted above, the communication and data processing system 30 of the storage device 10 processes information received or detected from the commercial medication package 50. The storage device 10 can process the information with or without additional information obtained by still other communications with other local and remote devices 40 and 60. The other devices can be local devices 40, such as a smart phone, tablet, pager, cell phone, interactive video device and conventional telephone, or remote devices 60, such as a server.

Figure 4:
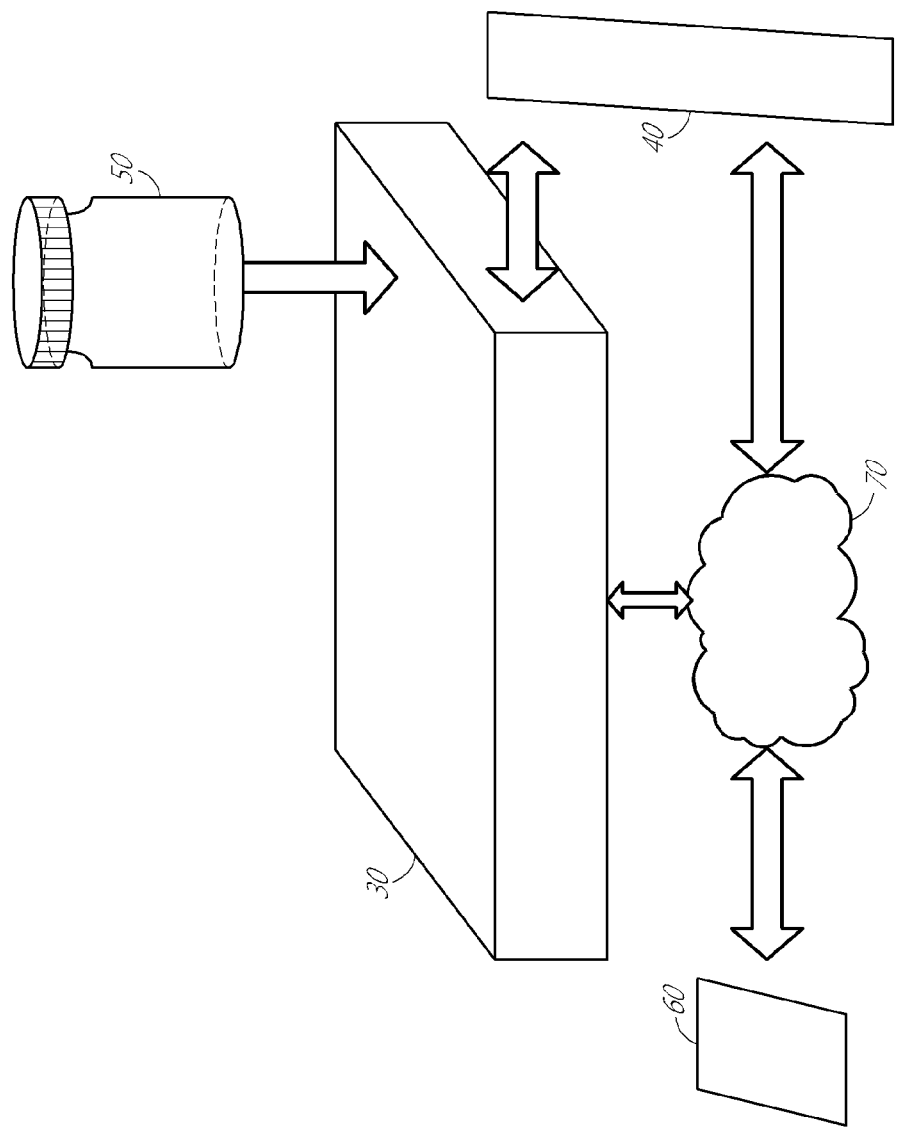
FIG. 4 is a network illustration of the exemplary communications of the medication storage device in accordance with an embodiment of the invention.

As shown in FIG. 4, the communication and data processing system 30 of the storage device 10 can receive or detect data from the barcode, quick response code, identification number or RFID chip of a commercial medication package 50, and can communicate directly with the local other devices 40, smart phones, tablets, pagers, cell phones, interactive video devices and conventional telephones, or indirectly, such as through a network 70 provided to communicate with remote other devices 60, such as the server, for bidirectional data exchange and communications regarding prescription and prescription regimen information, prescription content placement on the storage device 10, and user adherence to such prescription and prescription regimen information in response to the recognition of the commercial medication package 50. FIG. 4 is a network illustration of the exemplary communications of the medication storage device 10 in accordance with an embodiment of the invention. The communication and data processing system 30 of the storage device 10 can also be placed into and communicate data with a filling station (not shown) in the same manner as with the commercial package and local and remote devices described above.

The communications of the storage device 10 can be implemented using any of a wired or wireless communication link, LAN, WLAN, ISDN, X.25, DSL, and ATM type network or combination thereof for example, and others as specified under the IEEE 802 wireless standards, including but not limited to 802.11 (WiFi, WLAN), 802.15 (WPAN, Bluetooth, ZigBee) and 802.16 (WMAN). Connection to the local and remote devices 40 and 60, and the external data network 70 can include well-known methods such as RF, including 802.11 and Bluetooth standards, IRDA, various wireless data systems including pager networks, cellular packet data, and 20 and 30 systems, and physical serial connections such as the USB or Firewire standards.

The processor 34 can comprise a typical combination of hardware and software including system memory, operating system, application programs, graphical user interface (GUI), processor, and storage. Memory 36 can be provided as RAM, ROM, or similar memory, which can contain electronic information such as prescription and prescription regimen information, identification and location of compartments 12 on the storage device 10, data regarding opening and closing states of the compartments 12 and data regarding content level of the compartments 12. Based upon the detected prescription and prescription regimen information obtained from any of the content sensor 52 and cover sensor 18, commercial package 50, adjacent other device 40 and remote other device 60, the communication and data processing system 30 of the storage device 10 can calculate and identify compartments 12 in which to place a medication or from which to remove a medication, calculate and communicate adherence to a prescription regime, and store and update data of each.

The storage device 10 can be used for both manual and automated filling of medication. Since the storage device 10 contains medications in an ordered array with defined positions, automated filling and handling of orders is significantly enhanced over concepts intended for filling individual pill containers. That is, the storage device 10 can be filled from pre-mixed packets from a pharmacy, wherein for example, each packet coincides with a single compartment, so the filling process is the same, but simplified. Additionally, the storage device 10 can be plugged into a larger, automated filling station for automated filling. In this scenario, the filling station and the storage device 10 communicate with one another to establish the contents to be filled and the date/time for the usage of the content of each compartment. There are numerous physical and operative variations including but not limited to: total number of compartments, compartment highlight technique, interaction via direct input, interaction via smart phone/table, voice prompting. At the same time the storage device 10 is filled, information about the medications and prescription information can obtained and stored by the storage device 10.

Figure 5:
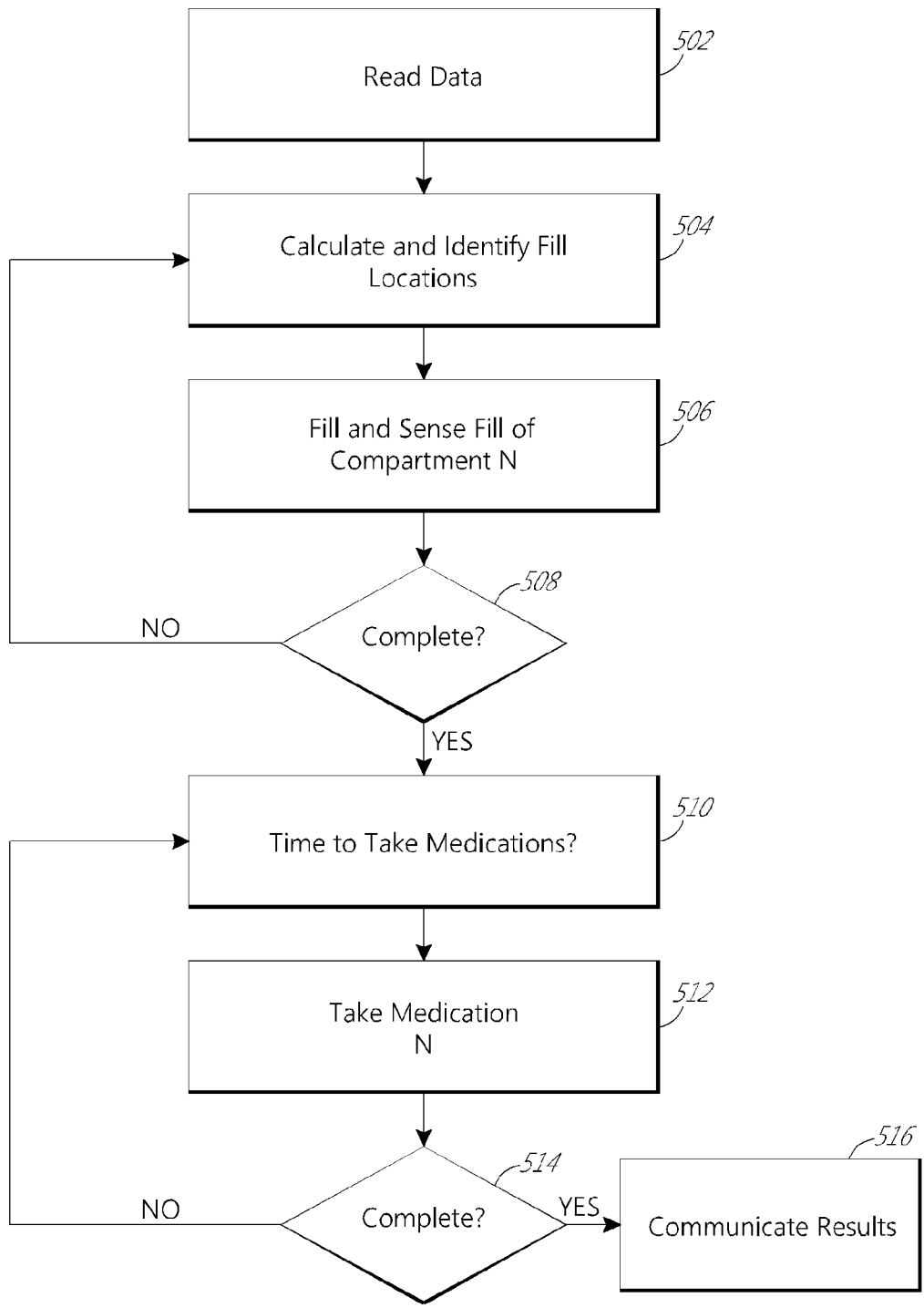
FIG. 5 illustrates a flow diagram of a method for utilizing the medication storage device in accordance with an embodiment of the invention.

FIG. 5 illustrates a flow diagram of a method for utilizing the medication storage device of FIG. 1 in accordance with an embodiment of the invention. Upon presentation of a new prescription, the medication storage device 10 reads identifying characteristics such as a barcode, RFID tag, quick response code or identification number or text of the commercial package 50 containing the new prescription at step 502 to obtain prescription information. Prescription information that can be obtained by the medication storage device 10 includes data about which medication is contained in each commercial package, which specific compartment 12 on the medication storage device 10 each medication occupies, the time and date the medication is to be taken, information about how to take the medication, and other information commonly found on conventional medication labels, including the date dispensed. Other prescription information that can be obtained by medication storage device 10 includes data which identifies who dispensed and/or prescribed the medications and the name of the facility and/or operator that provided the commercial package. Other prescription information can be received from the local devices 40, such as a smart phone, tablet, pager, cell phone, interactive video device and conventional telephone, or remote devices 60, such as the server.

Additional prescription information can also be included for the medication storage device 10 as a whole, including the identity of the individual patient, the range of dates for the medications included on the medication storage device 10, expiration or "use by" dates, and an identification number unique to that medication storage device 10 (e.g., serial number).

Each compartment 12 on the medication storage device 10 can contain a single medication or a plurality of different medications to be taken together at the same time, as prescribed by the healthcare service provider. FIG. 5 illustrates a flow diagram of a method for utilizing the medication storage device 10 in accordance with an embodiment of the invention. The method of FIG. 5 begins when the compartments 12 are to be filled with medicine. Prescription data is transferred in step 502 from the commercial packaging 50 to the medication storage device 10, via barcode, quick response code, identification number or RFID chip (including low-bit tags), or data port, where it is stored in memory. Other prescription information can be received from the local devices 40, such as a smart phone, tablet, pager, cell phone, interactive video device and conventional telephone, or remote devices 60, such as the server. The action of filling causes prescription data to be automatically transferred and stored to the medication storage device 10.

Once the prescription data is stored in memory of the storage device 10, the processor ascertains the medication regime, either from the prescription data or from communications received from the server 60 or elsewhere, and begins, at the appropriate times and in the appropriate manner, to alert the patient to fill the medication compartments 12 as directed at step 504. For example, upon presentation of a new prescription, the medication storage device 10 looks up the prescribed regimen and computes the set of locations or compartments 12 to which the medication should be stored for later dispensation.

The storage device 10 then identifies one compartment 12 at a time by activating the respective light emitting source 20 for the respective compartment 12 to be filled, and such that material of the cover 14 of the respective compartment 12 transmits the visible light of the light emitting source 20 throughout the respective cover 14 including the user-graspable end of each cover 14 which is visible in the slotted portion 28 of the body 22 even when both covers 14 and 24 are closed, thereby prompting the user to open, fill and close the identified compartment 12 at step 506. The storage device 10 can also identify the one compartment 12 at a time by providing information on the display 38 disposed on a surface of the cover 24.

The storage device 10 senses the open/close event of the compartment 12 and if desired, the actual fill of the compartment 12, and considers that compartment 12 to now be filled with the identified medication. The storage device 10 then identifies each subsequent compartment 12 in the same manner to be filled in turn, until all necessary compartments 12 have been filled at step 508. By looking up the regimen, computing the location and prompting the filling, one at a time, the storage device 10 lowers the burden of correct medication sorting, and accurate and timely dispensation for users and caregivers.

When the prescribed time to take a medication arrives, the storage device 10 can alert the patient to take a medication using acoustical, tactile and visual means or through wireless communications via pagers or other wireless devices 40 carried by the user at step 510. Patients can also see this and other important information on how to take the medications on the visual display of such devices 40 and on the display 38 of the storage device 10. The storage device 10 verifies that the proper medications are being taken at the proper times, and as much as possible, in the proper manner.

For example, when receiving and/or studying the prescription regimen and contents of the compartments 12, the storage device 10 computes the set of locations or compartments 12 from which the medication should be removed. The storage device 10 then identifies, by activating the respective light emitting source 20 for the respective compartment 12, one compartment 12 at a time, at step 512, prompting the user to open the cover 24 and the respective individual cover 14, remove medication from the identified compartment 12, and close the identified compartment 12. The storage device 10 senses the open/close event and, if desired, the actual remaining content level of the respective compartment 12. The storage device 10 then identifies each subsequent compartment 12 in the same manner from which the medication should be removed in turn, until all necessary medications have been removed at step 514.

If a patient opens the wrong compartment 12, the storage device 10 senses the open/close event, and if desired, can alert and guide the patient regarding replacement of the incorrect medication and selection of the correct medication by "flashing" the respective light emitting source 20 for the respective compartment 12 or of the correct compartment 12, or by flashing the light for the respective compartment 12 or of the correct compartment 12 in a red color, along with providing an audio alert. By looking up the regimen, computing the location and prompting the removal, one at a time, the storage device 10 lowers the burden of correct medication selection, and accurate and timely dispensation for users and caregivers.

At some point, time interval, content level, or as queried by the local and remote devices 40 and 60, the storage device 10 can communicate collected and processed assessment data through the network 70 to the service center or server 60 at step 516. This information can include the time and identities of medications taken from the storage device 10. If necessary, the service center server can send modifying medication use data to the storage device 10, and change or maintain the medication regimen for the patent. New medication use information can be conveyed to the patient, in the various different methods already described. For example, healthcare providers can communicate therapy, monitoring and behavioral changes, including modified medication use data using the data network back to the user via the storage device 10, or other user devices 40 such as a smart phone, tablet, pager, cell phone, interactive video device and conventional telephone described above.

As noted above, there are services that pre-pack custom mixes of pills and send them to the user or the pharmacy, and there are a number of devices that use small trays or compartments which are self-programmed by patients to remind them to take medications at a specific time, such as pill boxes at epill.com. All require manual filling and, when patients either self-program or self-fill the device, errors can occur. These errors become more common as the complexity of the medication regimen increases. Since these devices do not assist the user with identifying the medication, do not record or monitor medication usage, and are not connectable to an outside service or information provider, they have limited positive effect on medication adherence. Specifically, there are no devices that indicate which compartment to take or fill, and more specifically, there are no devices that indicate which compartment to take or fill using a light or other means to indicate the compartment of interest. Embodiments of the present invention can fulfill many of these unmet needs, and represent a significant improvement in patient care.

An advantage of embodiments of this invention over prior art is the dramatic simplification of the medication filling process. In prior devices, the user or caregiver must manually compute the correct medication locations and then fill them carefully to avoid mistakes. When a user has many simultaneous prescriptions, this can be a difficult and error prone process.

Prior art devices also require careful attention to detail when filling the device. Embodiments of the present invention can significantly reduce this burden by removing the mental effort and attention level required to prepare a weeklong complex polypharmacy regimen. This effort is reduced to the smallest possible unit of work and doesn't require knowledge of the full regimen or planning on the part of the user or caregiver.

The present invention has been described with reference to certain exemplary embodiments thereof. However, it will be readily apparent to those skilled in the art that it is possible to embody the invention in specific forms other than those of the exemplary embodiments described above. This can be done without departing from the spirit and scope of the invention. The exemplary embodiments are merely illustrative and should not be considered restrictive in any way.

What is claimed is:

1. A medication storage system, comprising:
   a medication storage container comprising:
      a plurality of storage compartments for receiving one or more medications;
      one or more indicators associated with each storage compartment, each indicator configured to indicate a selected one of the plurality of storage compartments;
   an identification sensor configured to read a code associated with medication prescription information; and
   a processor configured to:
      determine a medication regimen based on the detected medication prescription information, the medication regimen comprising a schedule for when a patient should take one or more doses of medication;
      determine storage compartments in which medications have been placed; and
      activate one or more of the indicators associated with a selected one of the plurality of storage compartments based on the schedule and the determined storage compartments.

2. The medication storage system of claim 1, further comprising one or more sensors configured to detect one or more of a content level of one or more of the storage containers and a movement of a cover of one or more of the storage containers.

3. The medication storage system of claim 2, wherein the one or more sensors comprise one or more of electronic switches, mechanical switches, and optical sensing devices.

4. The medication storage system of claim 2, wherein the processor is further configured to determine adherence to a medication regimen based on detecting a change in content level of one or more of the storage containers or detecting a movement of a cover of one or more of the storage containers.

5. The medication storage container of claim 2, wherein the processor is further configured to activate one or more of the indicators if it is detected that a cover of a storage compartment is opened at a time at which medication within the storage compartment is not scheduled to be taken.

6. The medication storage system of claim 1, wherein the medication storage container further comprises a communication interface configured to communicate data with one or more external devices.

7. The medication storage system of claim 6, wherein the data comprises one or more of: medication prescription information, medication regimens, location of medication in the medication storage container, and medication regimen adherence.

8. The medication storage system of claim 1, wherein the identification sensor comprises one or more of a barcode scanner or an RFID scanner.

9. The medication storage system of claim 1, wherein the processor is further configured to determine one or more of the plurality of storage compartments in which to place medication.

10. The medication storage system of claim 1, wherein the indicators comprise one or more light emitting sources.

11. An electronic method for operating a medication storage container, comprising:
receiving medication prescription information;
determining by a processor a medication regimen based on the received medication prescription information, the medication regimen comprising a schedule for when a patient should take one or more doses of medication;
determining one or more storage compartments of a plurality of storage compartments of the medication storage container in which medications have been placed, each storage compartment having one or more indicators associated therewith, each indicator configured to indicate a selected one of the plurality of storage compartments; and
activating one or more of the indicators associated with a selected one of the plurality of storage compartments based on the schedule and the determined storage compartments.

12. The method of claim 11, further comprising detecting by a sensor a content level of one or more of the storage compartments of the medication storage container.

13. The method of claim 11, further comprising detecting by a sensor a movement of a cover of one or more of the storage compartments.

14. The method of claim 13, further comprising activating one or more of the indicators if it is detected that a cover of a storage compartment is opened at a time at which medication within the storage compartment is not scheduled to be taken.

15. The method of claim 11, further comprising determining by a processor one or more storage compartments in which to place medication.

16. The method of claim 15, further comprising activating one or more of the indicators based on the determined compartments in which to place medication.

17. The method of claim 16, further comprising sensing a content level of one or more of the storage compartments and a movement of a cover of one or more of the storage compartments to determine if a medicine from within the one or more storage compartments has been removed.

18. The method of claim 11, further comprising recording regimen medication adherence data based on the detecting the content level of one or more of the storage compartments or the movement of a cover of one or more of the storage compartments.

19. The method of claim 11, further comprising determining by a processor adherence to a medication regimen.

20. The method of claim 11, further comprising receiving data from an external device, the data comprising one or more of: medication prescription information, medication regimens, location of medication in the medication storage container, and medication regimen adherence.

21. The method of claim 11, further comprising transmitting data to an external device, the data comprising one or more of: medication prescription information, medication regimens, location of medication in the medication storage container, and medication regimen adherence.

22. The method of claim 11, further comprising communicating with an automated filling station through a communication interface.

23. A medication storage container, comprising:
a transceiver configured to wirelessly connect with one or more electronic devices;
a plurality of storage compartments for receiving one or more medications;
one or more indicators associated with each storage compartment, each indicator configured to indicate a selected one of the plurality of storage compartments; and
a processor configured to:
determine a medication regimen based on medicine prescription information received by the medication storage container, the medication regimen comprising a schedule for when a patient should take one or more doses of medication;
determine storage compartments in which to place medication based on the schedule; and
activate one or more indicators associated with a selected one of the plurality of storage compartments based on the schedule and the determined storage compartments.

24. The medication storage container of claim 23, further comprising an identification sensor configured to detect the medication prescription information.

25. The medication storage container of claim 24, wherein the transceiver is configured to receive the medication prescription information from one or more of the identification sensor and the one or more electronic devices.

26. The medication storage container of claim 23, wherein the transceiver is configured to transmit data regarding the location of medication in the medication storage container and medication regimen adherence to the one or more electronic devices.

* * * * *